United States Patent [19]

Shibahara et al.

[11] Patent Number: 4,898,858
[45] Date of Patent: * Feb. 6, 1990

[54] CEPHALOSPORIN DERIVATIVES AND ANTIBIOTICS CONTAINING THE SAME

[75] Inventors: Seiji Shibahara, Tokyo; Tsuneo Okonogi, Kanagawa; Yasushi Murai, Kanagawa; Toshiaki Kudo, Kanagawa; Takashi Yoshida, Tokyo; Ken Nishihata, Kanagawa; Shinichi Kondo, Kanagawa, all of Japan

[73] Assignees: Meiji Seika Kaisha Ltd.; Susumu Mitsuhashi, both of Tokyo, Japan

[ * ] Notice: The portion of the term of this patent subsequent to Mar. 7, 2006 has been disclaimed.

[21] Appl. No.: 928,955

[22] Filed: Nov. 10, 1986

[30] Foreign Application Priority Data

Nov. 27, 1985 [JP] Japan .................. 60-267984

[51] Int. Cl.$^4$ ................ C07D 501/136; A61K 31/545
[52] U.S. Cl. ..................................... 514/206; 540/225
[58] Field of Search ................. 540/225, 227; 514/206

[56] References Cited

U.S. PATENT DOCUMENTS 4,621,081  11/1986  O'Callahan et al. ............... 540/225
4,810,702  3/1989  Shiba Hara et al. ............... 540/222

Primary Examiner—Nicholas S. Rizzo
Attorney, Agent, or Firm—Jordan and Hamburg

[57] ABSTRACT

New cephalosporin derivatives of a general formula (I) and non-toxic salts and non-toxic esters thereof are provided:

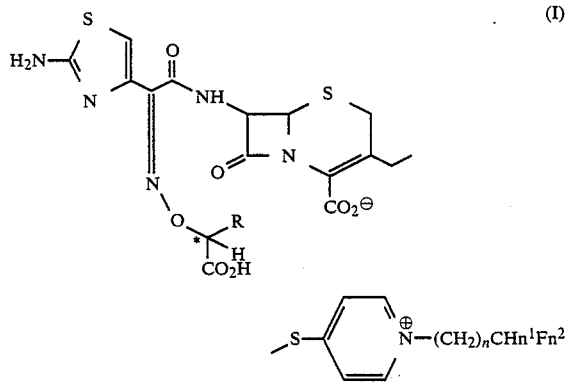

(wherein R represents an acyclic or cyclic lower alkyl group having 1–6 carbon atoms, which may optionally be substituted by a halogen atom; the steric configuration as asterisked (*) includes an optical-active (R)-form or (S)-form or an optical-inactive (RS)-form; n is 0 or 1, $n^1$ is 0 to 3, $n^2$ is 0 to 3; and when $n^1$ is 0, $n^2$ is 3; when $n^1$ is 1, $n^2$ is 2; when $n^1$ is 2, $n^2$ is 1; when $n^1$ is 3, $n^2$ is 0).

The new derivatives of the formula (I) and non-toxic salts and esters thereof have high bactericidal activity with broad antibacterial spectra, and these are useful as active ingredients in bactericides.

14 Claims, No Drawings

CEPHALOSPORIN DERIVATIVES AND ANTIBIOTICS CONTAINING THE SAME

FIELD OF THE INVENTION

The present invention relates to novel cephalosporin compounds having a 1-alkylpyridinium-4-ylthiomethyl group in the 3-position and an acyl group or a branched 1-alkyl-1-carboxymethoxyiminoaminothiazoleacetic acid in the 7-position as well as to antibiotics containing the compound.

BACKGROUND OF THE INVENTION

Cephalosporins have widely been utilized as antibiotics for mammals including humans. Various studies have extensively been made in this technical field for the purpose of intensifying the effectiveness and the safety of the cephalosporin antibiotics, and the outlines are described say in "Penicillin and Cephalosporin" (written by Edwin H. Flynn and published by Academic Press Co., in 1972) or "Structure Activity Relationships among the semisynthetic Antibiotics" (written by D. Perlman and published by Academic Press Co., in 1977). According to the disclosure of these publications, various kinds of cephalosporin-type compounds having an increased anti bacterial activity may be obtained by introducing various kinds of substitutes in the 7-acyl group or 3-substituent in the compounds.

For example, the introduction of an acyl group as derived from an α-alkoxyiminoaminothiazoleacetic acid into the 7-position of cephalosporin compounds has been noticed in these years, and U.S. Pat. Nos. 4,098,888 and 4,166,115 and British Patent No. 2,022,090 describe compounds having a residue derived from an α-methoxyiminoaminothiazoleacetic acid, and in addition, German Patent No. 2,921,316 describes compounds having a residue derived from an α-dimethylcarbomethoxyiminoaminothiazoleacetic acid. Thus, various studies have widely been made in this technical field to vary the part of the alkoxy-substituent in the α-alkoxyimino part of the aminothiazoleacetic acid residue in the cephalosporin compounds.

On the other hand, the introduction of residues of various kinds of heterocyclic compounds in the 3-positioned substituent of cephalosporin compounds has heretofore been tried. However, there are only some few compounds into which a pyridinium quaternary salt residue is introduced via a sulfur atom in the form of a 1-alkylpyridinium-4-ylthiomethyl group, and Japanese Patent Application OPI No. 90590/83 and No. 89289/80 describes some of these compounds. (The term "OPI" as used herein means an "unexamined published application"). These compounds are insufficient in the anti-bacterial activity and have some problems in the actual and practical use thereof. In order to solve the problem of the compounds in the practical use, the present inventors have prepared new cephalosporin compounds having a 1-fluoroethylpyridinium-4-ylthiomethyl group in the 3-position and have already filed a prior patent application of Japanese Patent Application. No. 254517/84. Afterwards, the present inventors have further made various studies on the point of the stereochemical configuration of the alkoxyimino part in the 7-side position of the cephem nucleus of the cephalosporin compounds and have found new compounds having an improved anti bacterial activity against antibiotic-resistant bacteria and having an increased practical usability, and thus have solved the problems now in question.

SUMMARY OF THE INVENTION

Accordingly, one subject matter of the present invention is to provide new cephalosporin derivatives of a general formula (I) and non-toxic salts and non-toxic esters thereof:

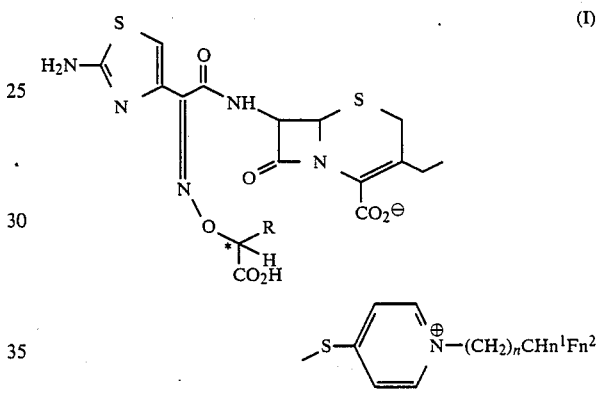

(wherein R represents an acyclic or cyclic lower alkyl group having 1–6 carbon atoms, which may optionally be substituted by a halogen atom; the steric configuration as asterisked (*) includes an optical active (R)-form or (S)-form or an optical-inactive (RS)-form; n is 0 or 1, $n^1$ is 0 to 3, $n^2$ is 0 to 3; and when $n^1$ is 0, $n^2$ is 3; when $n^1$ is 1, $n^2$ is 2; when $n^1$ is 2, $n^2$ is 1; when $n^1$ is 3, $n^2$ is 0).

Another subject matter of the present invention is to provide bactericides containing a component selected from the new caphalosporin derivatives of the general formula (I) and non-toxic salts or non-toxic esters thereof, as an active ingredient.

DETAILED DESCRIPTION OF THE INVENTION

Examples of the compounds of the present invention, as represented by the above general formula (I), are given below.

Example-1

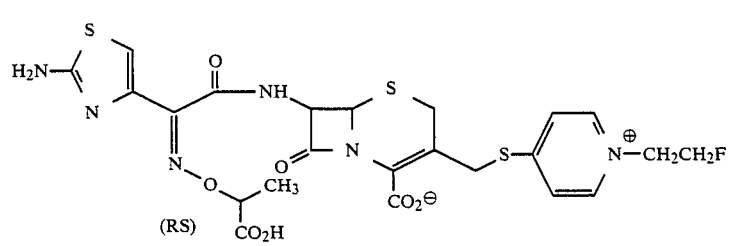

-continued
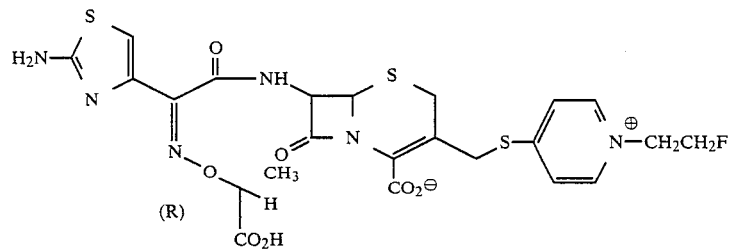
Example-2
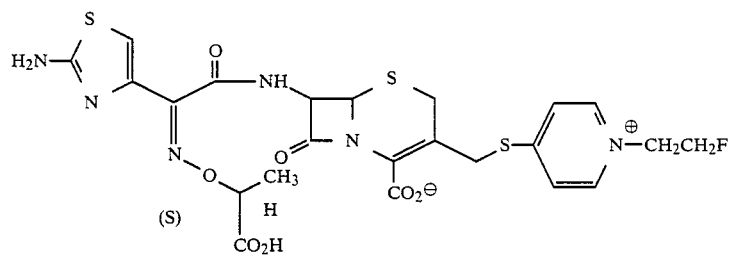
Example-3
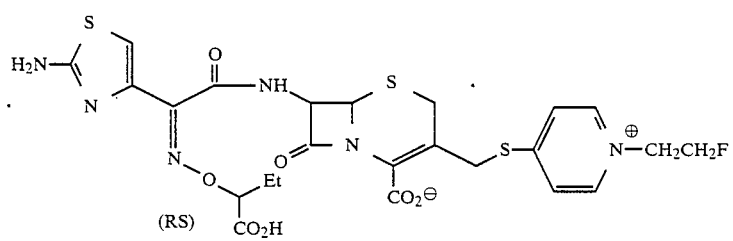
Example-4
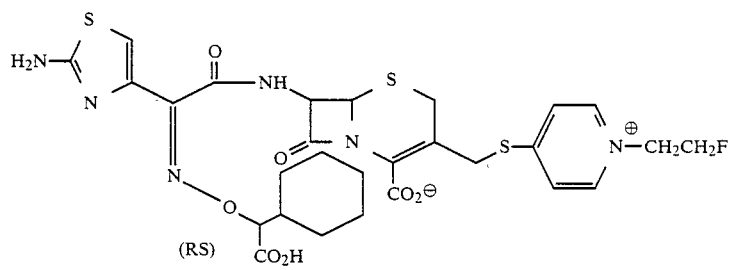
Example-5
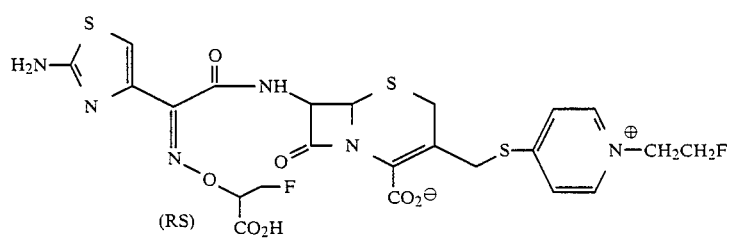
Example-6
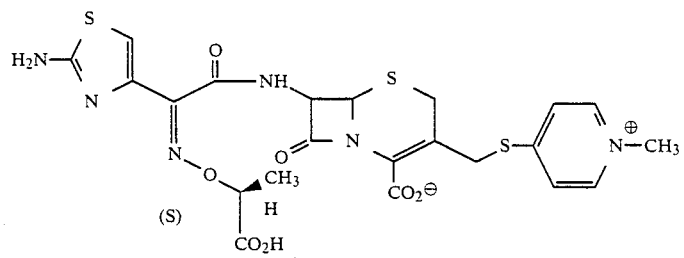
Example-7

-continued

Example-8

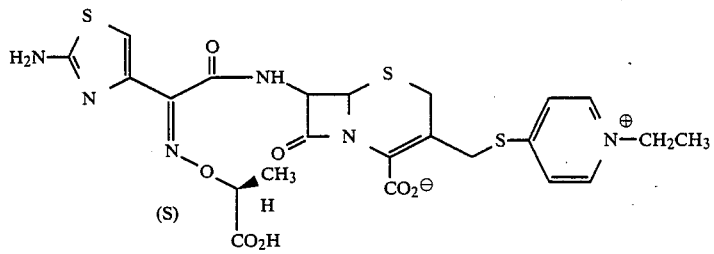

Example-9

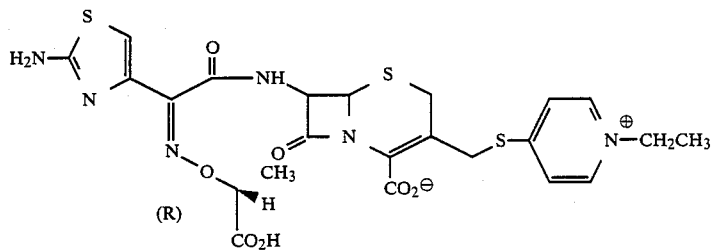

Example-10

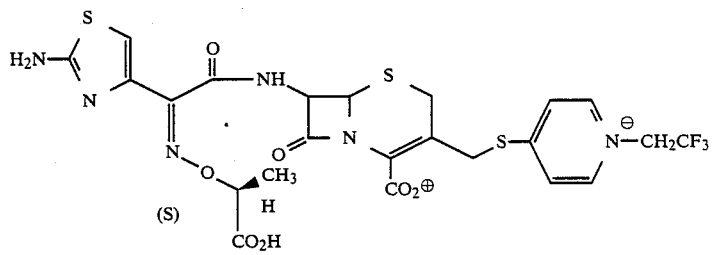

Example-11

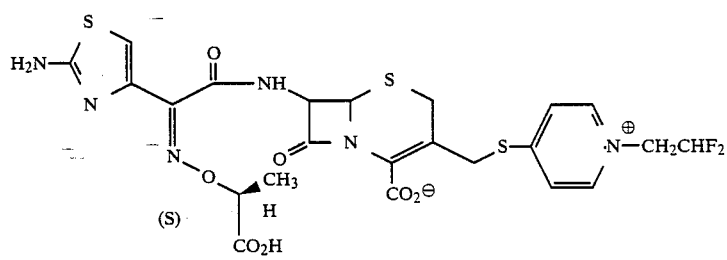

The compounds of the general formula (I) of the present invention may be obtained, for example, as follows:

1. Formation of compounds to be introduced into the 7- positioned side chain in the formula (I):

The compounds may be obtained according to any of the following processes (A), (B) and (C).

(A) In case the asterisked (*) part in the compounds of the formula (I) is an (RS)-form, the compounds are formed as shown in the following reaction formula, in accordance with the method of Belgian Patent No. 823,651:

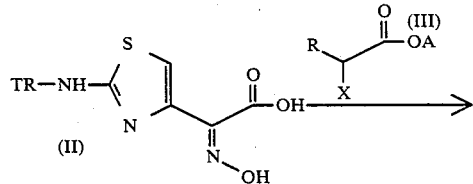

-continued

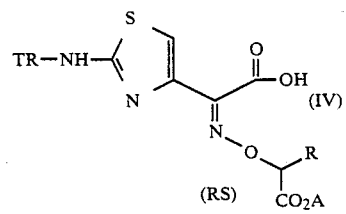

(In the reaction formula, TR represents an triphenylmethyl group, A represents a carboxylic acid-protective group, X represents a halogen atom, and R has the same meaning as above.)

According to the above reaction formula, an α-hydroxyiminoaminothiazoleacetic acid derivative of the formula (II) is reacted with an α-halocarboxylic acid derivative of the formula (III), which has a desired alkyl group R, in the presence of a strong base, to obtain a compound of the formula (IV) having the R-group in the alkoxime part therein. The compound (IV) is optionally subjected to optical resolution, to obtain its optical-active (R)-form and (S)-form. As the case may be, the carboxylic acid of the starting compound (II) is preferably optionally protected.

(B) In case the asterisked (*) part in the compounds of the formula (I) is an optical-active (R)-form or (S)-form and these optical active compounds (I) are to be directly obtained, an optical-active α-hydroxycarboxylic acid of the formula (V) having a desired alkyl group R is used, and this acid (V) is reacted with an alcohol in accordance with Mitsunobu Reaction, which is a general dehydration reaction between an alcohol and an acidic group.

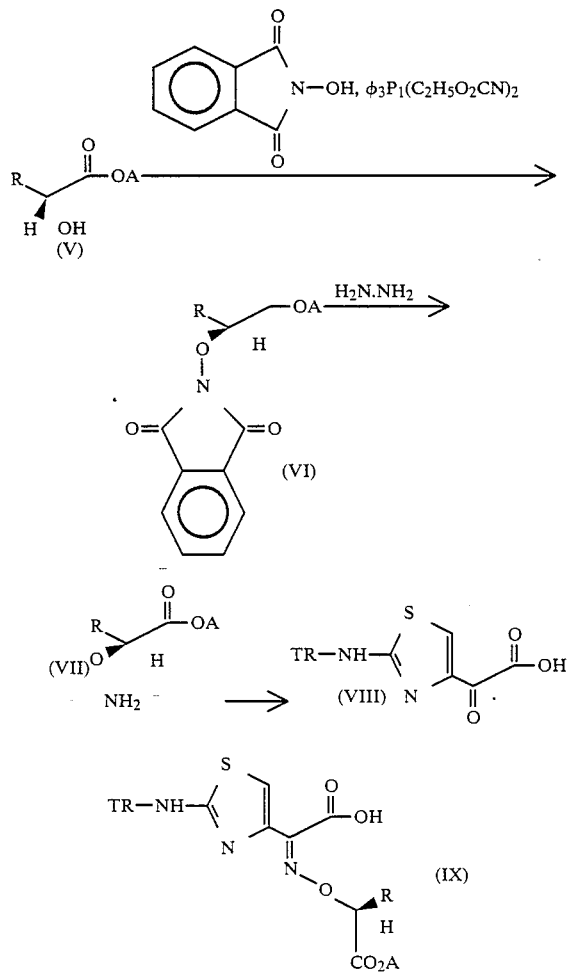

(In the reaction formula, φ represents a phenyl group, and R, TR and A have the same meanings as above.)

According to the above reaction formula, a compound of the formula (V) is reacted with N-hydroxyphthalimide in the presence of triphenylphosphine and diethyl azodicarboxylate by dehydration reaction, to obtain an N-alkoxyphtalimide derivative of the formula (VI). This derivative (VI) is treated with hydrazine to remove the phthaloyl group therefrom, to obtain an 0-alkylhydroxyamine derivative of the formula (VII). Next, this compound (VII) is reacted with an α-oxoaminothiazoleacetic acid derivative of the formula (VIII) to obtain an optically active aminothiazoleacetic acid derivative of the formula (IX) where the foot part of the alkyl group R is optically active.

The compounds of the formula (VIII) to be used in the above reaction may be obtained according to the method as illustrated in Japanese Patent Application OPI No. 10899/77.

(C) The optical active compounds of the formula (IX) may be obtained according to another method, using the compound of the formula (II) and the compound of the formula (V), as follows:

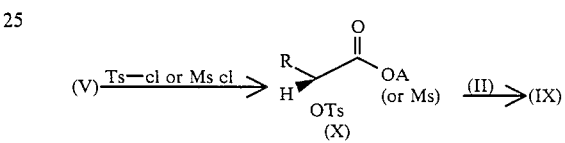

(In the reaction formula, Ts represents a toluenesulfonic acid group, Ms represents a methanesulfonic acid group, and R and A have the same meanings as above.)

According to the above reaction formula, an alcohol of the formula (V) is treated with a toluenesulfonic acid chloride (Ts-Cl) or a methanesulfonic acid chloride (Ms-Cl) in the presence of a base to obtain a toluenesulfonate or methanesulfonate of the formula (X). Next, the resulting ester (X) is reacted with a compound of the formula (II) in the presence of a base to obtain the desired product of the formula (IX).

In the above methods (B) and (C), the case where the asterisked (*) part in the compound of the formula (IX) has an (S)-configuration is specially mentioned. In the same manner, in case a starting compound of the formula (V) which has the other (R)-configuration is used, another compound of the formula (IX) which has the (R)-configuration may be obtained under the same reaction condition.

2. Formation of the products of the formula (I):
The compounds of the formula (I) may be obtained according to the following method (D) or (E):

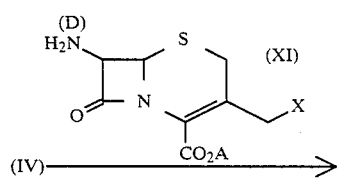

-continued

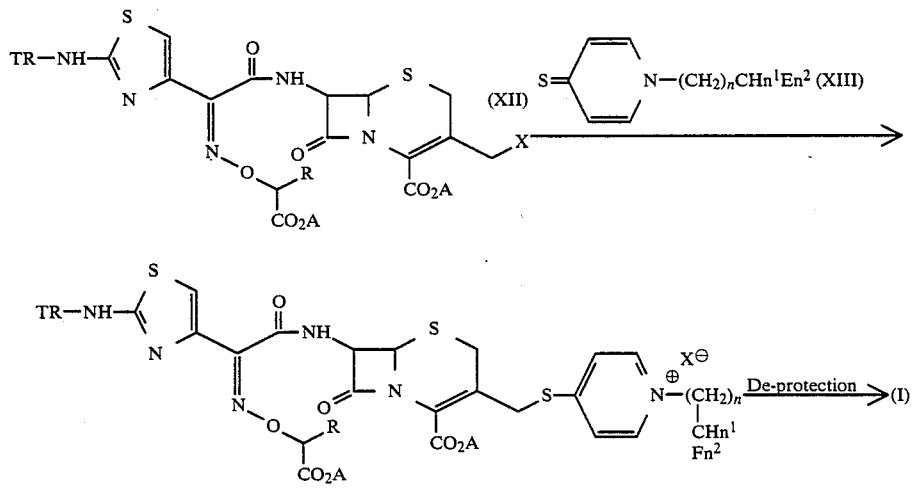

(In the reaction formula, R, TR, A, X, n, $n^1$ and $n^2$ have the same meanings as above.)

According to the above reaction formula, the compound of the formula (IV) is condensed with a 7-amino-3-halogenomethylcephalosporin derivative of the formula (XI) to obtain a compound of the formula (XII). Next, this compound (XII) is reacted with a desired pyridothione derivative of the formula (XIII) by substitution-reaction to obtain a compound of the formula (XIV). In the final, the protective groups in the resulting compound (XIV) are removed to obtain the compound of the formula (I) of the present invention.

In the above-steps, the methods for the formation of the compounds of the formulae (XII) and (XIV) are per se known, which are illustrated say in Japanese Patent Application OPI No. 090590/83. Regarding the formation of the compounds of the formulae (XIII) and (XIV), the present inventors have concurrently filed another Japanese Patent Application No. 024184/85 to claim the methods therefor.

In case the compound of the formula (IX) is used as the starting compound in the present reaction, the corresponding compound of the formula (I) may be obtained in the same manner.

(E) In the above method (D), the aminothiazole derivative is first introduced into the 7-amino group of the cephalosporin compound and then the 3-positioned group in the resulting intermediate is reacted with the pyridothione derivative. In some other cases, this reaction order is often preferably reversed, as follows:

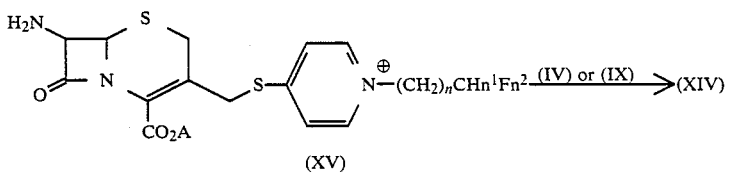

(In the reaction formula, A, $n^1$ and $n^2$ have the same meanings as above.)

The resulting compound of the formula (XIV) is deprotected in the same manner as the process (D), to obtain the aimed product of the formula (I) of the present invention.

The compounds of the formula (XV) as obtained in the above process are illustrated in the present inventors' own Japanese Patent Application No. 024184/85.

The compounds of the present invention thus obtained are important antibiotics which may be applied to mammals including humans, perorally or non-perorally.

In case the compounds of the present invention are to be used as a bactericide, for example, against human infectious disease, the compound is perorally or nonperorally administered in an amount of one dose/adult of 50–1500 mg, preferably 100–1000 mg, two times to six times a day.

The bactericides of the present invention are, in general, composed of the compound of the formula (I) of the present invention and a solid or liquid vehicle. Regarding the form of the preparations, the present bactericidal compositions are manufactured in the form of solid preparations such as tablets, capsules or powders or of liquid preparations such as injections, suspensions or syrups. Any known solid or liquid vehicles may be used for the formation of these preparations, which are generally used in this technical field.

The effect of the present invention will be described below.

The compounds of the formula (I) of the present invention have high bactericidal activity with broad bactericidal spectra, and the bactericidal spectra of some typical compounds of the present invention against various pathogenic bacteria in vitro are given in the following Table-1, as represented by the minimum growth-inhibitory concentration (MIC).

TABLE 1

| Tested bacteria | | Compound of Example 1 | Compound of Example 2 | Compound of Example 3 | Compound of Example 4 | Compound of Example 5 | Compound of Example 6 | Compound of Example 7 | Compound of Example 8 | Compound of Example 9 |
|---|---|---|---|---|---|---|---|---|---|---|
| Staphylococcus aureus | 606 | 3.13 | 6.25 | 3.13 | 6.25 | 3.13 | 3.13 | 3.13 | 1.56 | 6.25 |
| Staphylococcus aureus | 606 E-25 | 3.13 | 6.25 | 3.13 | 6.25 | 3.13 | 3.13 | 3.13 | 3.13 | 6.25 |
| Staphylococcus aureus | 209P JC-1 | 3.13 | 3.13 | 1.56 | 6.25 | 1.56 | 1.56 | 1.56 | 1.56 | 3.13 |
| Streptococcus faecalis | W-75 | 3.13 | 3.13 | 1.56 | 6.25 | 3.13 | 3.13 | 1.56 | 0.78 | 6.25 |
| Escherichia coli | ML1410 | 0.10 | 0.20 | 0.10 | 0.39 | 3.13 | 0.10 | 0.10 | 0.10 | 0.10 |
| Escherichia coli | NIHJ JC-2 | 0.10 | 0.10 | 0.10 | 0.39 | 3.13 | 0.05 | 0.10 | 0.10 | 0.10 |
| Escherichia coli | No.29 | 0.10 | 0.10 | 0.10 | 0.39 | 3.13 | 0.10 | 0.10 | 0.10 | 0.10 |
| Klebsiella pneumoniae | GN-69 | <0.025 | 0.05 | 0.05 | 0.10 | 1.56 | <0.025 | <0.025 | <0.025 | 0.05 |
| Klebsiella pneumoniae | GN-118 | <0.025 | 0.05 | <0.025 | 0.10 | 1.56 | <0.025 | <0.025 | <0.025 | 0.05 |
| Salmonella typhimurium | LT-2 | <0.025 | 0.05 | <0.025 | 0.20 | 3.13 | <0.025 | <0.025 | <0.025 | 0.05 |
| Salmonella enteritidis | No.11 | <0.025 | <0.025 | <0.025 | <0.025 | 0.20 | 0.05 | <0.025 | <0.025 | <0.025 |
| Proteus vulgais | GN-76 | 0.05 | 0.10 | 0.05 | 0.05 | 0.78 | 0.05 | 0.025 | 0.025 | 0.10 |
| Proteus vulgais | GN-76/C-1 | 0.10 | 0.10 | 0.05 | 0.20 | 0.78 | 0.10 | 0.05 | 0.05 | 0.10 |
| Proteus morganii | 1510 | 1.56 | 1.56 | 1.56 | 3.13 | 6.25 | 0.78 | 1.56 | 0.78 | 0.78 |
| Proteus rettgeri | GN-624 | 0.05 | 0.10 | 0.05 | 0.05 | 0.39 | <0.025 | <0.025 | 0.05 | <0.025 |
| Proteus rettgeri | J-0026 | 0.10 | 0.20 | 0.10 | 0.78 | 3.13 | 0.20 | 0.10 | 0.05 | 0.20 |
| Enterobacter Cloacae | G-0005 | 0.05 | 0.20 | 0.05 | 0.05 | 3.13 | 0.05 | 0.05 | 0.05 | 0.10 |
| Enterobacter Cloacae | G-0008 | 0.10 | 0.20 | 0.10 | 0.39 | 3.13 | 0.10 | 0.10 | 0.05 | 0.10 |
| Serratia marcescens | GN-10857 | 0.78 | 3.13 | 0.78 | 3.13 | 6.25 | 1.56 | 0.39 | 0.39 | 1.56 |
| Serratia marcescens | GN-629 | 0.10 | 0.39 | 0.20 | 0.78 | 6.25 | 0.20 | 0.10 | 0.10 | 0.39 |
| Pseudomonas aeruginosa | GN-10362 | 1.56 | 3.13 | 1.56 | 3.13 | 12.5 | 3.13 | 0.78 | 1.56 | 3.13 |
| Pseudomonas aeruginosa | MB-3833 | 1.56 | 3.13 | 1.56 | 3.13 | 12.5 | 1.56 | 0.78 | 0.78 | 3.13 |
| Pseudomonas aeruginosa | E-2 | 1.56 | 3.13 | 1.56 | 3.13 | 12.5 | 1.56 | 0.78 | 0.78 | 1.56 |

The compounds of the present invention have been obtained as the result of the stereochemical investigation on the alkoxyimino part in the 7-positioned substituent of the cephem nucleus of cephalosporin compounds, as described above. It has heretofore been said, that the bactericidal activity of cephalosporin compounds will increase because of the increment of the bulkiness of the substituent B of the alkoxyimino part in the compounds, as represented by:

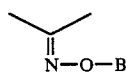

Despite of such conventional knowledge, the present inventors have found that the increment of the bactericidal activity of cephalosporin compounds apparently results from the stereochemical factor of the part of the substituent B. More precisely, the bactericidal activity of the compounds increases in the order of (S)-form>(RS)-form>(R)-form. This fact is proved by the above-described Table-1, and further, this is more apparently clarified by the following Table-2. The Table-2 shows the result of the comparison of the bactericidal activity of the compounds in which B represents —CH$_2$—COOH,

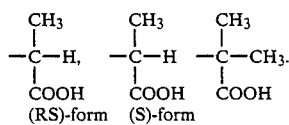

From the interpretation of the bulkiness of the substituent B, the bactericidal activity of the compound in which B is

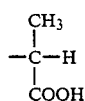

is theoretically to be middle between the compound in which B is —CH$_2$—COOH and that in which B is

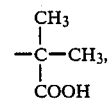

and in fact, the optically inactive compound with (RS)-configuration was actually found to follow this theory, in the experiment by the present inventors. However, the compound with (S)-configuration was found to have a higher bactericidal activity than the compound in which B is more bulky or

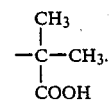

TABLE 2

MIC-value of the compounds of the present invention and the relevant compounds

MIC-value (γ/ml)

| Tested bacteria | B = —CH$_2$—COOH | $\begin{array}{c}CH_3\\|\\-C-H\\|\\COOH\end{array}$ (RS)-form | $\begin{array}{c}CH_3\\|\\-C\quad H\\|\\COOH\end{array}$ (S)-form | $\begin{array}{c}CH_3\\|\\-C-CH_3\\|\\COOH\end{array}$ |
|---|---|---|---|---|
| *Proteus vulgaris* GN76/C-1 | 0.39 | 0.10 | 0.05 | 0.10 |
| *Pseudomonas aeniginosa* | 6.25 | 1.56 | 0.78 | 1.56 |

Regarding the toxicity of the compounds of the present invention, the result in the acute toxicity test where the compound was applied to mice by intravenous injection proved that LD$_{50}$ of the compounds was 3 g/kg or more.

The present invention will be explained in greater detail by reference to the following examples, which, however, are not intended to be interpreted as limiting the scope of the present invention.

Referential Example 1:

(a) Diphenylmethyl (2R)-2-(phenoxyacetyloxy) propionate:

4.00 g (15.6 mmol) of diphenylmethyl (2S)-2-hydroxypropionate, 2.49 g (15.6 mmol) of phenoxyacetic acid and 4.90 g (18.7 mmol) of triphenylphosphine were dissolved in 100 ml of THF, and after cooled with ice, 2.96 ml (18.7 mmol) of diethyl azodicarboxylate was added thereto and the whole was stirred for 1 hour at the same temperature.

The solvent was distilled out, and the residue was purified by silicagel-chromatography (solvent: toluene), to obtain 5.70 g of the above-entitled compound.

$^1$H-NMR (90 MHz, CDCl$_3$, δppm): 1.47 (3H,d,J=6.8 Hz), 4.62(2H,s), 5.30 (1H,q,J=6.8 Hz), 6.84 (1H,s), 6.70–7.40 (15H,m) [α]$_D$+29 (C=5.0 CHCl$_3$)

(b) Diphenylmethyl (2R)-2-hydroxypropionate:

5.70 g (14.6 mmol) of diphenylmethyl (2R)-2-(phenoxyacetyloxy)propionate was dissolved in 40 ml of methanol, 0.7 ml of 25%-aqueous ammonia was added thereto and the whole was stirred for 1 hour at room temperature, and thereafter 1N-HCl was added thereto to adjust the pH value thereof to 7.0 and the solvent was distilled out therefrom.

The residue was dissolved in ethyl acetate, washed with water, dried and concentrated and thereafter purified by silicagel-chromatography (toluene/ethyl acetate=10/1) to obtain 2.71 g of the above-entitled compound.

$^1$H-NMR (90 MHz, CDCl$_3$, δppm): 1.42 (3H,d,J=6.8 Hz), 2.76 (1H,s), 4.33 (1H,q,J=6.8 Hz), 6.89 (1H,s), 7.10–7.40 (10H,m) [α]$_D$+9.1 (C=5.00, CHCl$_3$)

(c) Diphenylmethyl (2S)-2-phthaloyloxypropionate:

2.27 g (8.86 mmol) of diphenylmethyl (2R)-2-hydroxypropionate, 1.44 g (8.86 mmol) of N-hydroxyphtalimide and 2.78 g (10.6 mmol) of triphenylphosphine were dissolved in 70 ml of THF, and after cooled with ice, 1.68 ml (10.6 mmol) of diethyl azodicarboxylate was added thereto and stirred for 3 hours at the same temperature and then concentrated. The residue was purified by silicagel-chromatography (toluene/ethyl acetate=5/1), to obtain 3.20 g of the above-entitled compound.

$^1$H-NMR (90 MHz, CDCl$_3$, δppm): 1.64 (3H,d,J=6.8 Hz), 5.02 (1H,q,J=6.8 Hz), 6.89 (1H,s), 7.10–7.80 (14H,m) [α]$_D$-59 (C=5.0, CHCl$_3$)

(d) 2-(2-tritylamino-4-thiazolyl)-2-(1S)-(1-diphenylmethoxycarobnyl)ethoxyimino acetic acid-syn isomer:

1.0 g (2.49 mmol) of diphenylmethyl (2S)-phthaloyloxypropionate was dissolved in 80 ml of THF, and THF, and 122 μl (2.49 mmol) of hydrazine (monohydrate) was added thereto and stirred for 1 hour at room temperature, and after cooled with ice, 0.4 ml of 6N-HCl aqueous solution was added thereto and further stirred for 30 minutes at the same temperature and then filtrated.

20 ml of methanol and 1.03 g (2.49 mmol) of 2-(2-tritylamino-4-thiazolyl)glyoxalic acid were added to the resulting filtrate and stirred for 3 hours, while the pH value of the solution was adjusted to 4.5–5.5.

The reaction solution was concentrated and the resulting residue was dissolved in ethyl acetate, and after the solution was washed with an acidic water (pH 2.0), this was concentrated to 15 ml and crystallized to obtain 1.2 g of the above-entitled compound.

$^1$H-NMR (90 MHz, CDCl$_3$, δppm): 1.50 (3H,d,J=7.0 Hz), 5.07 (1H,q,J=7.0 Hz), 6.64 (1H,s), 6.88 (1H,s), 7.10–7.50 (25H,m) [α]$_D$-10.2 (C=5.0, CHCl$_3$)

Referential Example 2:

(a) Diphenylmethyl (2R)-2-phthaloyloxypropionate:

According to the treatment of the step (c) in the Referential Example 1, diphenylmethyl (2S)-2-hydroxypropionate was used and the above-entitled compound was obtained.

[α]$_D$+63(C=5.0, CHCl$_3$)

(b) (2-tritylamino-4-thiazolyl)-2-{(1R)-(1-diphenylmethoxycarbonyl)ethoxyimino}acetic acid-syn isomer:

According to the treatment of the step (d) in the Referential Example 1, diphenylmethyl (2R)-2-phthaloyloxypropionate was used and the above-entitled compound was obtained.

[α]$_D$+10.0(C=5.0, CHCl$_3$)

Referential Example 3:

(a) Diphenylmethyl (2S)-2-(p-toluenesulfonyloxy)propionate:

1 g (4.0 mmol) of diphenylmethyl (2S)-2-hydroxypropionate was dissolved in 10 ml of methylene chloride, and 1.29 ml (16 mmol) of pyridine and 2.3 g (12 mmol) of tosyl chloride were added thereto, while cooled with ice, and reacted for one night at room temperature. The solvent was removed out and the resulting residue was dissolved in ethyl acetate, washed with water, 1N-HCl and aqueous sodium bicarbonate solution, and dried, concentrated and then purified by silicagel-chromatography (toluene) to obtain 1.31 g of the above-entitled compound.

$^1$H-NMR (90 MHz, CDCl$_3$, δppm): 1.50 (3H,d,J=7 Hz), 2.35 (3H,s), 5.05(1H,q,J=7 Hz), 6.85 (1H,s), 7.05–7.75 (14H,m)

(b) Allyl 2-(2-tritylamino-4-thiazolyl)-2-(1R)-(1-diphenylmethoxycarobnyl)ethoxyimino acetate-syn isomer:

1.30 g (3.17 mmol) of diphenylmethyl (2S)-2-(p-toluenesulfonyloxy)propionate and 0.74 g (1.59 mmol) of allyl 2-(2-tritylamino-4-thiazolyl)-2-hydroxyiminoacetate-syn isomer were dissolved in 4.7 ml of DMF, and 0.66 g (4.8 mmol) of potassium carbonate was added thereto and reacted for one night. Ethyl acetate was added to the reaction solution, washed with water and 1N-HCl, and dried and concentrated and then purified by silicagel-chromatography (toluene/ethyl acetate=50/1) to obtain 0.75 g of the above-entitled compound.

$^1$H-NMR (90 MHz, CDCl$_3$, δppm): 1.50 (3H,d,J=7.0 Hz), 4.40–6.20 (6H,m), 6.65 (1H,s), 6.85 (1H,s), 7.10–7.50 (25H,m)

(c) 2-{(2-tritylamino-4-thiazolyl)-2-(1R -(1-diphenylmethoxycarbonyl)ethoxyimino} acetic acid-syn isomer:

750 mg (1.06 mmol) of allyl 2-(2-tritylamino-4-thiazolyl)-2-{(1R)-(1-diphenylmethoxycarbonyl) ethoxyimino}acetate-syn isomer was dissolved in 7.5 ml of methylene chloride, and 26 mg of triphenylphosphine and 26 mg of tetrakis(triphenylphosphine)palladium (0) were added thereto in N$_2$-stream. After complete dissolution, ethyl acetate solution containing 200 mg (1.1 mmol) of potassium 2-ethyl-hexanoate was added to the resulting solution and reacted for 10 minutes. After the reaction, the solvent was distilled out and isopropylether was added to obtain a precipitate. The precipitate formed was dissolved in ethyl acetate, and the pH value of the resulting solution was adjusted to 2, and the solution was washed with water and dried and then concentrated to obtain crystalline 700 mg of the above-entitled compound.

$^1$H-NMR (90 MHz, CDCl$_3$, δppm): 1.50 (3H,d,J=7 Hz), 5.05 (1H,q,J=7 Hz), 6.60 (1H,s), 6.85 (1H,s), 7.10–7.50 (25H,m)

Referential Example 4:

p-Methoxybenzyl 3-chloromethyl-7-[2-(2-tritylamino-4-thiazolyl)-2-{(diphenylmethoxycarbonyl)ethoxyimino}acetamido}-ceph-3-em-4-carboxylate-syn isomer:

97 mg (0.24 mmol) of p-methoxybenzyl 7-amino-3-chloromethyl-ceph-3-em-4-carboxylate hydrochloride and 120 mg (0.27 mmol) of 2-(2-tritylamino-4-thiaozlyl)-2-{diphenylmethoxycarbonyl)ethoxyimino}acetic acid-syn isomer were dissolved in 3 ml of methylene chloride, and 98 μl (1.2 mmol) of pyridine and 24 μl (0.27 mmol}of phosphorus oxychloride were added thereto, while cooled with ice, and reacted for 10 minutes.

After the reaction, 12 ml of chloroform was added and the resulting solution was washed twice with 6 ml of water and dried with magnesium sulfate and then, the solvent was distilled out. The resulting residue was purified by silicagel-chromatography (benzene/ethyl acetate=20/1) to obtain 180 mg of the above-entitled compound.

$^1$H-NMR (90 MHz, CDCl$_3$, δppm): 1.54,1.60 (3H,d,J=7.3 Hz), 3.10,3.30,3.45,3.57 (2H,ABq,J=18 Hz), 3.80 (3H,s), 4.31,4.37,4.58,4.60 (2H,ABq,J=12 Hz), 4.92,4.93 (1H,d,J=5 Hz), 5.00–5.30 (1H,m), 5.20 (2H,s), 5.87,5.91 (1H,dd,J-5 Hz8 Hz) 6.70 (1H,s), 6.80–7.50 (30H,m)

Referential Example 5:

p-Methoxybenzyl 7-2-(2-tritylamino-4-thiazolyl)-2-(diphenylmethoxycarbonylethoxyimino)acetamido}-3-[{1-(2-fluoroethyl)pyridinium}-4-ylthiomethyl]-ceph-3-em-4-carboxylate iodide:

157 mg (0.24 mmol) of p-methoxybenzyl 3-{1-(2-fluoroethyl)-pyridinium-4-ylthiomethyl}-7-amino-ceph-3-em-4-carboxylate iodide hydrochloride and 120 ml (0.27 mmol) 27 mmol) of 2-(2-tritylamino-4-thiazolyl)-2-{(diphenylmethoxycarbonyl) ethoxyimino}acetic acid-syn isomer were dissolved in 3 ml of methylene chloride, and 98 μl (1.2 mmol) of pyridine and 24 μl (0.27 mmol) of phosphorus oxychloride were added thereto, while cooled with ice, and reacted for 15 minutes. After the reaction, the solvent was distilled out and isopropylether was added to the resulting residue to form a precipitate. This precipitate was dried and then purified by silicagel-chromatography (chloroform/methanol=10/1) to obtain 200 mg of the above-entitled compound.

$^1$H-NMR (90 MHz, CDCl$_3$, δppm): 1.57 (3H,d,J=7.2 Hz), 3.35,3.50 (2H,ABq,J=18 Hz), 3.75 (3H,s), 4.35(2H,s), 4.50–5.20 (5H,m), 4.95,4.96 (1H,d,J=5 Hz), 5.16 (2H,s), 5.74,5.75 (1H,dd,J=5 Hz,8 Hz), 6.65 (1H,s), 6.70–7.30 (30H,m), 7.65,8.73 (4H,ABq,J=6.3 Hz)

Example 1:-

(6R,7R)-7-{(Z)-2-(2-Aminothiazol-4-yl)-2-(1-carboxyethoxyimino)acetamido}-3-[{1-(2-fluoroethyl) pyridinium}-4-ylthiomethyl]-ceph-3-em-4-carboxylate:

280 mg (0.28 mmol) of p-methoxybenzyl 3-chloromethyl-7-{(2-tritylamino-4-thiazolyl)-2-(1-diphenylmethoxycarbonyl-ethoxyimino)acetamido}-ceph-3-em-4-carboxylate-syn isomer was dissolved in 3 ml of acetone, and 1.0 ml of acetone solution containing 60 mg (0.4 mmol) of sodium iodide was added to the resulting solution at room temperature and reacted for 40 minutes. After the reaction, the solvent was distilled out, and methylene chloride was added to the resulting residue, the insoluble materials were filtered off, and the remaining filtrate was concentrated under reduced pressure, to obtain p-methoxybenzyl 3-iodomethyl-7- {2-(2-tritylamino-4-thiazolyl)-2-(1-diphenylmethoxycarbonyl-ethoxyimino)acetamido}-ceph-3-em- 4-carboxylate-syn isomer. To this was added 52 mg (0.34 mmol) of 1-(2-fluoroethyl)-4-pyridothione, and the resulting mixture was dissolved in 3 ml of chloroform and reacted for 1 hour at room temperature. After the reaction, the chloroform was distilled out under reduced pressure, and the residue was purified by silicagel-chromatography (chloroform/ethanol=10/1) and dissolved in 0.8 ml of anisol, and then, 4.0 ml of trifluoroacetic acid was added thereto, while cooled with ice, and reacted for 1 hour. After the reaction, isopropylether was added to the reaction solution to form a precipitate. After dried, 190 mg of a powder was obtained. To this was added 1 ml of water and the pH value of the resulting solution was adjusted to 7.8 with sodium hydrogencarbonate, and the solution was purified with HP-20 resin (methanol/H$_2$O=¼) to obtain 110 mg of the above-entitled compound.

$^1$H-NMR (90 MHz, D$_2$O, δppm): 1.40 (3H,d,J=6.8 Hz), 3.40,3.70 (2H,ABq,J=17.9 Hz), 4.25 (2H,s), 4.50–5.20 (5H,m), 5.17 (1H,d,J=4.6 Hz), 5.60–5.70 (1H,m), 6.84 (1H,s), 7.80,8.37 (4H,ABq,J=6.6 Hz)

Example 2:

(6R,7R)-7-[(Z)-2-(2-Aminothiazol-4-yl)-2-{(1R)-carboxyethoxyimino}acetamido]-3-[{1-(2-fluoroethyl)-pyridinium}-4-ylthiomethyl]-ceph-3-em-4-carboxylate:

140 mg (0.14 mmol) of p-methoxybenzyl 3-chloromethyl-7-[2-(2-tritylamino-4-thiazolyl)-2-{(1R)-diphenylmethoxycarbonyl-ethoxyimino}acetamido]-ceph-3-em- 4-carboxylate-syn isomer was dissolved in 1 ml of acetone, and 0.5 ml of acetone solution containing 30 mg (0.2 mmol) of sodium iodide was added to the resulting solution at room temperature and reacted for 40 minutes. After the reaction, the solvent was distilled out, methylene chloride was added to the resulting residue, the insoluble materials were filtrated out, and the remaining filtrate was concentrated under reduced pressure to obtain p-methoxybenzyl 3-iodomethyl-7-[2-(2-tritylamino-4-thiazolyl)-2-{(1R)-diphenylmethoxycarbonylethoxyimino}-ceph-3-em-4-carboxylate-syn isomer. To this was added 26 mg (0.17 mmol) of 1-(2-fluoroethyl)-4-pyridothione, and the resulting mixture was dissolved in 1 ml of chloroform and reacted for 1 hour at room temperature. After the reaction, the chloroform was distilled out under reduced pressure, and the resulting residue was purified by silicagel-chromatography (chloroform/methanol=10/1) and dissolved in 0.4 ml of anisole. To this was added 2.0 ml of trifluoroacetic acid, while cooled with ice, and reacted for 1 hour. After the reaction, isopropylether was added thereto to form a precipitate. After dried, 100 mg of a powder was obtained. To this was added 1 ml of water and the pH value of the resulting solution was adjusted to 7.8 with sodium hdyrogencarbonate, and the solution was purified with HP-20 resin (methanol/H$_2$O=¼) to obtain 60 mg of the above-entitled compound.

$^1$H-NMR (400 MHz, D$_2$O, δppm): 1.44 (3H,d,J=6.9 Hz), 3.50,3.73 (2H,ABq,J=17.9 Hz), 4.25,4.37 (2H,ABq,J=14.0 Hz), 4.63 (1H,q,J=6.9 Hz), 4.66–4.96 (4H,m), 5.20 (1H,d,J=4.6 Hz), 5.75 (1H,d,J=4.6 Hz), 6.96 (1H,s), 7.89,8.45 (4H,ABq,J=7.9 Hz)

Example 3:

(6R,7R)-7-[(Z)-2-(2-Aminothiazol-4-yl)-2-{(1S)-carboxyethoxyimino}acetamido]-3-[{1-(2-fluoroethyl)-pyridinium}-4-ylthiomethyl]-ceph-3-em-4-carboxylate:

300mg (0.29 mmol) of p-methoxybenzyl 3-chloromethyl-7-[2-(2-tritylamino-4-thiazolyl)-2-{(1S)-diphenylmethoxycarbonylethoxyimino}acetamido]-ceph-3-em-4-carboxylate was dissolved in 20 ml of acetone, and 1.0 ml of acetone solution containing 60 mg (0.44 mmol) of sodium iodide was added to the resulting solution at room temperature and reacted for 40 minutes. After the reaction, the solvent was distilled out, and methylene chloride was added to the resulting residue, the insoluble materials were filtrated out, and the remaining filtrate was concentrated under reduced pressure to obtain p-methoxybenzyl 3-iodomethyl-7-[2-(2-tritylamino-4-thiazolyl)-2-{(1S)-diphenylmethoxycarbonylethoxyimino}acetamido]-ceph-3-em-4-carboxylate-syn isomer. To this was added 45 mg (0.32 mmol) of 1-(2-fluoroethyl)-4-pyridothione and the resulting mixture was dissolved in 2 ml of chloroform and reacted for 1 hour at room temperature. After the reaction, the chloroform was distilled out under reduced pressure, and the residue was purified by silicagel-chromatography (chloroform/methanol=10/1) and dissolved in 0.5 ml of anisole, and then, 2.5 ml of trifluoroacetic acid was added thereto, while cooled with ice, and reacted for 1 hour. After the reaction, isopropylether was added to the reaction mixture to form a precipitate therein. After dried, 130 mg of a powder was obtained. To this was added 1 ml of water and the pH value of the resulting solution was adjusted to 7.8 with sodium hydrogencarbonate, and the solution was purified with HP-20 resin (methanol/H$_2$O=¼) to obtain 70 mg of the above-entitled compound.

$^1$H-NMR (400 MHz, D$_2$O, δppm): 1.45 (3H,d,J=7.2 Hz), 3.47,3.72 (2H,ABq,J=17.4 Hz), 4.21,4.36 (2H,ABq,J=13.8 Hz), 4.64 (1H,q,J=7.2 Hz, 4.73–4.96 (4H,m), 5.19 (1H,d,J=4.6 Hz), 5.79 (1H,d,J=4.6 Hz), 6.98 (1H,s), 7.86,8.46 (4H,ABq,J=6.9 Hz)

Example 4:

(6R,7R)-7-{(Z)-2-(2-Aminothaizol-4-yl)-2-(1-carboxypropyloxyimino)acetamido}-3-[{(1-(2-fluoroethyl)pyridinium}-4-ylthiomethyl]-ceph-3-em-4-carboxylate:

100 mg (0.1 mmol) of p-methoxybenzyl 3-chloromethyl-7-{2-(2-tritylamino-4-thiazolyl)-2-(1-diphenylmethoxycarbonylpropyloxyimino)acetamido}-ceph-3-em-4-carboxylate-syn isomer was dissolved in 1 ml of acetone, and 0.5 ml of acetone solution containing 28 mg (0.19 mmol) of sodium iodide was added to the resulting solution at room temperature and reacted for 40 minutes. After the reaction, the solvent was distilled out, methylene chloride was added to the residue, the insoluble materials were filtrated out, and the remaining filtrate was concentrated under reduced pressure, to obtain p-methoxybenzyl 3-iodomethyl-7-{2-(2-tritylamino-4-thiazolyl)-2-(1-diphenylmethoxycarbonyl-propyloxyimino) acetamido}-ceph-3-em-4-carboxylate-syn isomer. To this was added 18 mg (0.11 mmol) of 1-(2-fluoroethyl)-4-pyridothione, and the resulting mixture was dissolved in 1 ml of chloroform and reacted for 1 hour at room temperature. After the reaction, the chloroform was distilled out under reduced pressure, and the residue was purified by silicagel-chromatography (chloroform/methanol=10/1) and dissolved in 0.4 ml of anisole, and then 1.3 ml of trifluoroacetic acid was added thereto, while cooled with ice, and reacted for 1 hour. After the reaction, isopropylether was added to the reaction solution to form a precipitate therein. After dried, 80 mg of a powder was obtained. To this was added 1 ml of water and the pH value of the resulting solution was adjusted to 7.8 with sodium hydrogencarbonate, and the solution was purified with HP-20 resin (methanol/H$_2$O=¼) to obtain 45 mg of the above-entitled compound.

$^1$H-NMR (90 MHz, D$_2$O, δppm): 1.12 (3H,t,J=7.5 Hz), 1.97(2H,q,J=7.5 Hz), 3.61,3.62,3.91,3.92 (2H,ABq,J=18 Hz), 4.47 (2H,s), 4.62–5.42 (6H,m), 5.82–5.92 (1H,m), 7.06(1H,s), 7.98,7.99,8.56,8.57 (4H,ABq,J=6.9 Hz)

Example 5:

(6R,7R)-7-{(Z)-2-(2-Aminothiazol-4-yl)-2-(1-carboxy-1-cyclohexylmethoxyimino-aceta}-3-[{1-(2-fluoroethyl) pyridinium}-4-ylthiomethyl]-ceph-3-em-4-carboxylate:

40 mg (0.04 mmol) of p-methoxybenzyl 3-chloromethyl-7-{2-(2-tritylamino-4-thiazolyl)-2-(1-diphenylmethoxycarbonyl-1-cyclohexylme)acetamido}-ceph-3-em-4-carboxylate-syn isomer was dissolved in 1 ml of acetone, and 0.5 ml of acetone solution containing 11 mg (0.07 mmol) of sodium iodide was added to the resulting solution at room temperature and reacted for 40 minutes. After the reaction, the solvent was distilled out, methylene chloride was added to the resulting residue, the insoluble materials were filtrated out, and the remaining filtrate was concentrated under reduced pressure to obtain p-methoxybenzyl 3-iodomethyl-7-{2-(2-tritylamino-4-thiazolyl)-2-(1-diphenylmethoxycarbonyl-1-cyclohexylme)-acetamido}-ceph-3-em-4-carboylate-syn isomer. To this was added 7 mg (0.04 mmol) of 1-(2-fluoroethyl)-4-pyridothione, and the resulting mixture was dissolved in 1 ml of chloroform and reacted for 1 hour at room temperature. After the reaction, the chloroform was distilled out under reduced pressure, and the residue was purified by silicagel-chromatography (chloroform/methanol=10/1) and dissolved in 0.12 ml of anisole, and then, 0.4 ml of trifluoroacetic acid was added thereto, while cooled with ice, and reacted for 1 hour. After the reaction, isopropylether was added to the reaction solution to form a precipitate therein. After dried, 30 mg of a powder was obtained. To this was added 1 ml of water and the pH value of the resulting solution was adjusted to 7.8 with sodium hydrogencarbonate, and the solution was purified with HP-20 resin (methanol/H$_2$O=¼) to obtain 14 mg of the above-entitled compound.

$^1$H-NMR (90 MHz, D$_2$O, δppm): 1.08–2.08 (1H,m), 3.60,3.89 (2H,ABq,J=18 Hz), 4.38–4.58 (3H,m), 4.88–5.58 (4H,m), 5.36 (1H,d,J=4.5 Hz), 5.82,5.83 (1H,d,J=4.5 Hz), 7.06 (1H,s), 8.02,8.58 (4H,ABq,J=6.2 Hz)

Example 6:

(6R,7R)-7-{(Z)-2-(2-Aminothiazol-4-yl)-2-(1-carboxy-2-fluoroethoxyimino)acetamido-3-[{1-(2-fluoroethyl)pyridinium}-4-ylthiomethyl]-ceph-3-em-4-carboxylate:

130 mg (0.125 mmol) of p-methoxybenzyl 3-chloromethyl-7-{2-(2-tritylamino-4-thiazolyl)-2-(1-diphenylmethoxycarbonyl-2-fluoroethoxy) acetamido}-ceph-3-em-4-carboxylate-syn isomer was dissolved in 1 ml of acetone, and 0.5 ml of acetone solution containing 28 mg (0.19 mmol) of sodium iodide was added to the resulting solution at room temperature and reacted for 40 minutes. After the reaction, the solvent was distilled out, methylene chloride was added to the resulting residue, the insoluble materials were filtrated out, and the remaining filtrate was concentrated under reduced pressure to obtain p-methoxybenzyl 3-iodomethyl-7-{2-(2-tritylamino-4-thiazolyl)-2-(1-diphenylmethoxycarbonyl-2-fluoroethoxy)acetamido}-ceph-3-em-4-carboxylate-syn isomer. To this was added 23 mg (0.15 mmol) of 1-(2-fluoroethyl)-4-pyridothione, and the resulting mixture was dissolved in 1 ml of chloroform and reacted for 1 hour at room temperature. After the reaction, the chloroform was distilled out under reduced pressure, and the residue was purified by silicagel-chromatography (chloroform/methanol=10/1) and dissolved in 0.15 ml of anisole, and then, 1.5 ml of trifluoroacetic acid was added thereto, while cooled with ice, and reacted for 1 hour. After the reaction, isopropylether was added to the reaction solution to form a precipitate therein. After dried, 70 mg of a powder was obtained. To this was added 1 ml of water and the pH value of the resulting solution was adjusted to 7.8 with sodium hydrogencarbonate, and the solution was purified with HP-b 20 resin (methanol/H₂O=¼) to obtain 32 mg of the above entitled compound.

¹H-NMR (400 MHz, D₂O, δppm): 3.48,3.49,3.72 (2H,ABq,J=18.0 Hz), 4.22,4.23,4.40,4.41 (2H,ABq), 4.70-5.00 (7H,m), 5.20(1H,d,J=4.4 Hz), 5.76,5.79(1H,d,J=4.4 Hz), 7.02,7.03 (1H,s), 7.87, 8.46(4H,ABq,J=6.9 Hz)

Example 7:

(6R,7R)-7-[(Z)-2-(2-Aminothiazol-4-yl)-2-{(1S)-carboxyethoxyimino}acetamid]-3-(1-methylpyridinium-4-ylthiomethyl)-ceph-3-em-4-carboxylate:

150 mg (0.15 mmol) of p-methoxybenzyl 3-chloromethyl-7-[2-(2-tritylamino-4-thiazolyl)-2-{(1S)-diphenylmethoxycarobnylethoxyimino}-acetamido]-ceph-3-em-4-carboxylate-syn isomer was dissolved in 3 ml of acetone, and 1.0 ml of acetone solution containing 33 mg (0.22 mmol) of sodium iodide was added to the resulting solution at room temperature and reacted for 40 minutes. After the reaction, the solvent was distilled out, methylene chloride was added to the residue, the insoluble materials were filtrated out, and the remaining filtrate was concentrated under reduced pressure to obtain p-methoxybenzyl 3-iodomethyl-7-[2-(2tritylamino-4-thiaozlyl)-2- {(1S)-diphenylmethoxycarobnyl-ethoxyimino}-acetamido]-ceph-3-em-4-carboxylate-syn isomer. To this was added 21 mg (0.18 mmol) of 1-ethyl-4-pyridothione, and the resulting mixture was dissolved in 5 ml of chloroform and reacted for 1 hour at room temperature. After the reaction, the chloroform was distilled out under reduced pressure, and the residue was purified by silicagel-chromatography (chloroform/methanol=10/1) and dissolved in 0.2 ml of anisole, and then, 1.5 ml of trifluoroacetic acid was added thereto, while cooled with ice, and reacted for 1 hour. After the reaction, isopropylether was added to the reaction solution to form a precipitate therein. After dried, 100 mg of a powder was obtained. To this was added 1 ml of water and the pH value of the resulting solution was adjusted to 7.8 with sodium hydrogencarbonate, and the solution was purified with HP-20 resin (methanol/H₂O=¼) to obtain 49 mg of the above-entitled compound.

¹H-NMR (90 MHz, D₂O, δppm): 1.45 (3H,d,J=6.8 Hz), 3.42,3.72 (2H,ABq,J=17.6 Hz), 4.17 (3H,s), 4.28 (2H,s), 4.77 (1H,q,J=6.8 Hz), 5.20 (1H,d,J=4.6 Hz), 5.74 (1H,d,J=4.6 Hz) 6.93 (1H,s), 7.81,8.34 (4H,ABq,J=6.6 Hz)

Example 8:

(6R,7R)-7-[(Z)-2-(2-Aminothiazol-4-yl)-2-(1S)-carboxyethoxyimino}acetamido]-3-(1-ethylpyridinium 4-ylthiomethyl)-ceph-3-em-4-carboxylate:

150 mg (0.15 mmol) of p-methoxybenzyl 3-chloromethyl-7-[2-(2-tritylamino-4-thiazolyl)-2-{(1S)-diphenylmethoxycarbonylethoxyimino}-acetamido]-ceph-3-em-4-carboxylate-syn isomer was dissolved in 3 ml of acetone, and 1.0 ml of acetone solution containing 33 mg (0.22 mmol) of sodium iodide was added to the resulting solution at room temperature and reacted for 40 minutes. After the reaction, the solvent was distilled out, methylene chloride was added to the residue, the insoluble materials were filtrated out, and the remaining filtrate was concentrated under reduced pressure to obtain p-methoxybenzyl 3-iodomethyl-7-[2-(2-tritylamino-4-thiazolyl)-2-{(1S)-diphenylmethoxycarbonyl-ethoxyimino}acetamido]-ceph-3-em-4-carboxylate-syn isomer. To this was added 24 mg (0.18 mmol) of 1-ethyl-4-pyridothione, and the resulting mixture was dissolved in 1 ml of chloroform at room temperature and reacted for 1 hour. After the reaction, the chloroform was distilled out under reduced pressure, and the residue was purified by silicagel-chromatography (chloroform/methanol=10/1) and dissolved in 0.2 ml of anisole, and then, 1.5 ml of trifluoroacetic acid was added thereto, while cooled with ice, and reacted for 1 hour. After the reaction, isopropylether was added to the reaction solution to form a precipitate therein. After dried, 93 mg of a powder was obtained. To this was added 1 ml of water and the pH value of the resulting solution was adjusted to 7.8 with sodium hydrogencarbonate, and the solution was purified with HP-20 resin (methanol/H₂O=¼) to obtain 55 mg of the above-entitled compound.

¹H-NMR (90 MHz, D₂O, δppm): 1.46 (3H,d,J=6.8 Hz), 1.55 (3H,t,J=7.2 Hz), 3.43,3.73 (2H,ABq,J=18 Hz), 4.27 (2H,s), 4.39 (2H,q,J=7.2 Hz), 4.63 (1H,q,J=6.8 Hz, 5.16 (1H,d,J=4.6 Hz), 5.70 (1H,d,J=4.6 Hz), 6.85 (1H,s), 7.77,8.37 (4H,ABq,J=6.6 Hz)

Example 9:

(6R,7R)-7-[(Z)-2-(2-Aminothiazol-4-yl)-2-{(1R)-carboxyethoxyimino}acetamid]-3-(1-ethylpyridinium-4-ylthiomethyl)-ceph-3-em-4-carboxylate:

190 mg (0.19 mmol) of p-methoxybenzyl 3-chloromethyl-7-[2-(2-tritylamino-4-thiazolyl)-2-{(1R)-diphenylmethoxycarbonylethoxyimino}-acetamido]-ceph-3-em-4-carboxylate-syn isomer was dissolved in 3 ml of acetone, and 0.1 ml of acetone solution containing 43 mg (0.29 mmol) of sodium iodide was added to the resulting solution at room temperature and reacted for 40 minutes. After the reaction, the solvent was distilled out, methylene chloride was added to the residue, the insoluble materials were filtrated out, and the remaining filtrate was concentrated under reduced pressure, to obtain p-methoxybenzyl 3-iodomethyl-7-[2-(2-tritylamino-4-thiazolyl)-2-{(1R)-diphenylmethoxycarbonyl-ethoxyiminno}acetamido]-ceph-3-em-4-carboxylate-syn isomer. To this was added 27 mg (0.21 mmol) of 1-ethyl-4-pyridothion, and the resulting mixture was dissolved in 3 ml of chloroform and reacted for 1 hour at room temperature. After the reaction, the chloroform was distilled out under reduced pressure, and the residue was purified by silicagel-chromatography (chloroform/methanol=10/1) and dissolved in 0.2 ml of anisole, and then, 2.0 ml of trifluoroacetic acid was added thereto, while cooled with ice, and reacted for 1 hour. After the reaction, isopropylether was added to the reaction solution to form a precipitate therein. After dried, 100 mg of a powder was obtained. To this was added 1 ml of water and the pH value of the resulting solution was adjusted to 7.8 with sodium hydrogencarbonate, and the solution was purified with HP-20 resin (methanol/H₂O=¼) to obtain 65 mg of the above-entitled compound.

¹H-NMR (90 MHz, D₂O, δppm): 1.43 (3H,d,J=6.8 Hz), 1.53 (3H,t,J=7.1 Hz), 3.45,3.73 (2H,ABq,J=17.1 Hz), 4.26 (2H,s), 4.38 (2H,q,J=7.1Hz), 4.60 (1H,q,J=6.8 Hz), 5.17 (1H,d,J=4.6 Hz), 5.65 (1H,d,J=4.6 Hz), 6.82 (1H,s), 7.77,8.34 (4H,ABq,J=6.8 Hz)

Example 10:

(6R,7R)-7-[(Z-2-(2-Aminothiazol-4-yl)-2-{(1S)-carboxyethoxyimino}acetamido]-3-[{1-(2,2,2-trifluoroethyl)pyridinium}-4-ylthiomethyl]-ceph-3-em-4-carboxylate:

100 mg (0.098 mmol) of p-methoxybenzyl 3-chloromethyl-7-[2-(2-tritylamino-4-thiazolyl)-2-{(1S)-diphenylmethoxycarbonylethoxyimino}acetamido]-ceph-3-em-4-carboxylate-syn isomer was dissolved in 1 ml of acetone, and 0.5 ml of acetone solution containing 29 mg (0.20 mmol) of sodium iodide was added to the resulting solution at room temperature and reacted for 40 minutes, After the reaction, the solvent was distilled out, methylene chloride was added to the residue, the insoluble materials were filtrated out, and the remaining filtrate was concentrated under reduced pressure, to obtain p-methoxybenzyl 3-iodomethyl-7-[2-(2-tritylamino-4-thiazolyl)-2-{(1S)-diphenylmethoxycarbonyl-ethoxyimino}acetamido]-ceph-3-em-4-carboxylate-syn isomer. To this was added 23 mg (0.12 mmol) of 1-(2,2,2-trifluoroethyl)-4-pyridothione, and the resulting mixture was dissolved in 1 ml of chloroform and reacted for 1 hour at room temperature. After the reaction, the chloroform was distilled out under reduced pressure, and the residue was purified by silicagel-chromatography (chloroform/methanol=10/1) and dissolved in 0.34 ml of anisole, and then, 1.13 ml of trifluoroacetic acid was added thereto, while cooled with ice, and reacted for 1 hour. After the reaction, isopropylether was added to the reaction solution to form a precipitate therein. After dried, 73 mg of a powder was obtained. To this was added 1 ml of water and the pH value of the resulting solution was adjusted to 7.8 with sodium hydrogencarbonate, and the solution was purified with HP-20 resin (methanol/$H_2O=\frac{1}{4}$) to obtain 55 mg of the above-entitled compound.

$^1$H-NMR (90 MHz, $D_2O$, δppm):
1.58 (3H,d,J=6.6 Hz), 3.56,3.88 (2H,ABq,J=18 Hz), 4.46 (2H,s), 4.68–5.58 (3H,m), 5.33 (1H,d,J=4.5 Hz), 5.86 (1H,d,J=4.5 Hz), 7.05 (1H,s), 8.04,8.62 (4H,ABq,J=6.9 Hz)

Example 11:
(6R,7R)-7-[(Z)-2-(2-Aminothiazol-4-yl)-2-{(1S)-carboxyethoxyimino}acetamido]-3-[{1-(2,2-difluoroethyl)pyridinium}-4-ylthiomethyl]-ceph-3-em-4-carboxylate:

140 mg (0.14 mmol) of p-methoxybenzyl 3-chloromethyl-7-[2-(2-tritylamino-4-thiazolyl)-2-{(1S)diphenylmethoxycarbonylethoxyimino}acetamido]-ceph-3-em-4-carboxylate-syn isomer was dissolved in 1 ml of acetone, and 0.5 ml of acetone solution containing 30 mg (0.2 mmol) of sodium iodide was added to the resulting solution at room temperature and reacted for 40 minutes. After the reaction, the solvent was distilled out, methylene chloride was added to the residue, the insoluble materials were filtrated out, and the remaining filtrate was concentrated under reduced pressure, to obtain p-methoxybenzyl 3-iodomethyl-7-[2-(2-tritylamino-4-thiazolyl)-2-{(1S)-diphenylmethoxycarbonylethoxyimino}acetamido]-ceph-3-em-4-carboxylate-syn isomer. To this was added 30 mg (0.17 mmol) of 1-(2,2-difluoroethyl)-4-pyridothione, and the resulting mixture was dissolved in 1 ml of chloroform and reacted for 1 hour at room temperature. After the reaction, the chloroform was distilled out under reduced pressure, and the residue was purified by silicagel-chromatography (chloroform/methanol=10/1) and dissolved in 0.4 ml of anisole, and then, 2.0 ml of trifluoroacetic acid was added thereto, while cooled with ice, and reacted for 1 hour. After the reaction, isopropylether was added to the reaction solution to form a precipitate therein. After dried, 110 mg of a powder was obtained. To this was added 1 ml of water and the pH value of the resulting solution was adjusted to 7.8 with sodium hydrogencarbonate, and the solution was purified with HP-20 resin (methanol/$H_2O=\frac{1}{4}$) to obtain 55 mg of the above-entitled compound.

$^1$H-NMR (90 MHz, $D_2O$, δppm): 1.50 (3H,d,J=7.0 Hz), 3.50,3.80 (2H,ABq,J=18 Hz), 4.40 (2H,s), 4.60–5.55 (4H,m), 5.25 (1H,d,J=4.5 Hz), 5.80 (1H,d,J=4.5 Hz), 7.03 (1H,s), 7.94,8.52 (4H,ABq,J=6.9 Hz)

Example 12:
Preparation for injection:
A sterilized injection containing 1000 mg (titer) of the compound of the Example 3 was filled in one vial. Example 13:

| Capsules: | |
| --- | --- |
| Compound of Example 3 | 250 parts (titer) |
| Lactose | 60 parts |
| Magnesium stearate | 5 parts |

These were uniformly blended, and the resulting mixture was encapsulated in an amount of 250 mg (titer) capsule.

Example 14:
Soft capsules for rectal application:
25 parts (titer) of the compound of the Example 3 were added to a uniform base comprising:

| Olive oil | 160 parts |
| --- | --- |
| Polyoxyethylene-laurylether | 10 parts |
| Sodium hexametaphosphate | 5 parts. |

The resulting mixture was uniformly blended and encapsulated to obtain soft capsules for rectal application each containing 250 mg (titer)/capsule.

What is claimed is:
1. Cephalosporin derivatives of a general formula (I) and non-toxic salts and non-toxic esters thereof:

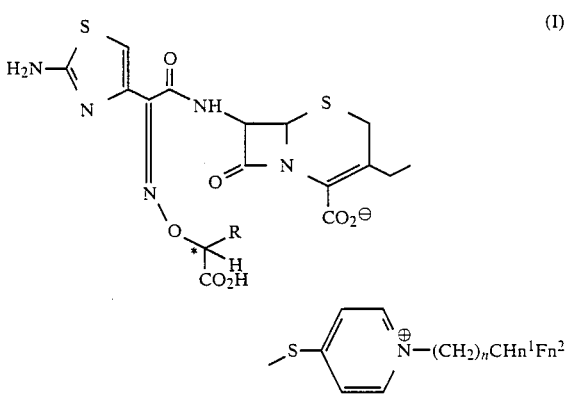

(wherein R represents an acyclic or cyclic lower alkyl group having up to 6 carbon atoms, which may optionally be substituted by a halogen atom; the steric configuration as asterisked (*) includes an optical-active (R)-form or (S)-form or an optical-inactive (RS)-form; n is 0 or 1, $n^1$ is 0 to 3, $n^2$ is 0 to 3; and when $n^1$ is 0, $n^2$ is 3; when $n^1$ is 1, $n^2$ is 2; when $n^1$ is 2, $n^2$ is 1: when $n^1$ is 3, $n^2$ is 0).

2. (6R,7R)-7-{(Z)-2-(2-aminothiazol-4-yl)-2-(1-carboxyethoxyimino)acetamido}-3-[{1-(2-fluoroethyl)pyridinium}-4-ylthiomethyl]-ceph-3-em-4-carboxylate according to claim 1.

3. (6R,7R)-7-[(Z)-2-(2-aminothiazol-4-yl)-2-{(1R)-carboxyethoxyimino}acetamido]-3-[{1-(2-fluoroethyl)pyridinium}-4-ylthiomethyl]-ceph-3-em-4-carboxylate according to claim 1.

4. (6R,7R)-7-[(Z)-2-(2-aminothiazol-4-yl)}-2-{(1S)-carboxyethoxyimino}acetamido]-3-[{1-(2-fluoroethyl)pyridinium}-4-ylthiomethyl]-ceph-3-em-4-carboxylate according to claim 1.

5. (6R,7R)-7-{(Z)-2-(2-aminothiazol-4-yl)-2-(1-carboxypropyloxyimino)acetamido}-3-[{1-(2-fluoroethyl)pyridinium}-4-ylthiomethyl]-ceph-3-em-4-carboxylate according to claim 1.

6. (6R,7R)-7-[{(Z)-2-(2-aminothiazol-4-yl)-2-(1-carboxy-1-cyclohexylmethoxyimino)acetamido}-3-[{(1-(2-fluoroethyl)pyridinium}-4-ylthiomethyl]-ceph-3-em-4-carboxylate according to claim 1.

7. (6R,7R)-7-{(Z)-2-(2-aminothiazol-4-yl)-2-(1-carboxy-2-fluoroethoxyimino)acetamido}-3-[{1-(2-fluoroethyl)pyridinium}-4-ylthiomethyl]-ceph-3-em-4-carboxylate according to claim 1.

8. (6R,7R)-7-[(Z)-2-(2-aminothiazol-4-yl)-2-{(1S)-carboxyethoxyimino}acetamido]-3-(1-methylpyridinium-4-ylthiomethyl)-ceph-3-em-4-carboxylate according to claim 1.

9. (6R,7R)-7-[(Z)-2-(2-aminothiazol-4-yl)-2-{(1S)-carboxyethoxyimino}acetamido]-3-(1-ethylpyridinium-4-ylthiomethyl)-ceph-3-em-4-carboxylate according to claim 1.

10. (6R,7R)-7-[(Z)-2-(2-aminothiazol-4-yl)-2-{(1R)-carboxyethoxyimino}-acetamido-3-(1-ethylpyridinium-4-ylthiomethyl)-ceph-3-em-4-carboxylate according to claim 1.

11. (6R,7R)-7-[(Z)-2-(2-aminothiazol-4-yl)-2-{(1S)-carboxyethoxyimino}acetamido]-3-[{1-(2,2,2-trifluoroethyl)-pyridinium}-4-ylthiomethyl]-ceph-3-em-4-carboxylate according to claim 1.

12. (6R,7R)-7-[(Z-2-(2-aminothiazol-4-yl)-2-{(1S)-carboxyethoxyimin}acetamido]-3-[{(1-(2,2-difluoroethyl) pyridinium-4-ylthiomethyl]-ceph-3-em-4-carboxylate according to claim 1.

13. A bactericide containing a pharmaceutical carrier or excipient and an effective amount of a material selected from cephalosporin derivatives of a formula (I) and non-toxic salts and non-toxic esters thereof:

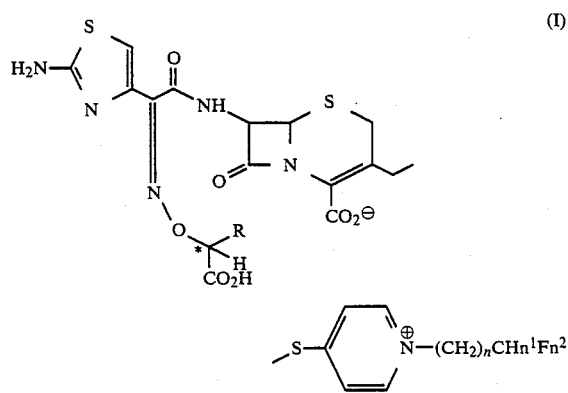

(wherein R represents an acyclic or cyclic alkyl group having up to 6 carbon atoms, which may optionally be substituted by a halogen atom; the steric configuration as asterisked (*) includes an optical-active (R)-form or (S)-form or an optical-inactive (RS)-form; n is 0 or 1, $n^1$ is 0 to 3, $n^2$ is 0 to 3; and when $n^1$ is 0, $n^2$ is 3; when $n^1$ is 1, $n^2$ is 2; when $n^1$ is 2, $n^2$ is 1; when $n^1$ is 3, $n^2$ is 0).

14. A bactericide containing a pharmaceutical carrier or excipient and an effective amount of an active ingredient of the compound as claimed in any one of claims 2–12.

* * * * *